(12) United States Patent
Srinivasan et al.

(10) Patent No.: US 11,285,257 B2
(45) Date of Patent: Mar. 29, 2022

(54) PEN NEEDLE MAGAZINE

(71) Applicant: Becton, Dickinson and Company, Franklin Lakes, NJ (US)

(72) Inventors: Sudarsan Srinivasan, North Brunswick, NJ (US); Cole Constantineau, Cambridge, MA (US); Michel Bruehwiler, Newton, MA (US); Tyson Montidoro, Davie, FL (US); Jeffrey Chagnon, Somerville, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 384 days.

(21) Appl. No.: 16/094,765

(22) PCT Filed: Mar. 31, 2017

(86) PCT No.: PCT/US2017/025274
§ 371 (c)(1),
(2) Date: Oct. 18, 2018

(87) PCT Pub. No.: WO2017/189164
PCT Pub. Date: Nov. 2, 2017

(65) Prior Publication Data
US 2019/0125957 A1 May 2, 2019

Related U.S. Application Data

(60) Provisional application No. 62/328,655, filed on Apr. 28, 2016.

(51) Int. Cl.
*A61M 5/00* (2006.01)
*A61M 5/32* (2006.01)
(Continued)

(52) U.S. Cl.
CPC .............. *A61M 5/002* (2013.01); *A61M 5/24* (2013.01); *A61M 5/32* (2013.01); *A61M 5/3202* (2013.01);
(Continued)

(58) Field of Classification Search
CPC ........ A61M 5/24; A61M 5/32; A61M 5/3202; A61M 5/3297; A61M 5/3298; A61M 5/34;
(Continued)

(56) References Cited

U.S. PATENT DOCUMENTS 5,829,589 A 11/1998 Nguyen et al.
5,873,462 A 2/1999 Nguyen et al.
(Continued)

FOREIGN PATENT DOCUMENTS

EP 2119423 A1 11/2009
EP 2420270 A2 2/2012
(Continued)

OTHER PUBLICATIONS

Li-Yuan Chang et al., "Integrated Flow Sensing for Focal Biochemical Stimulation", Proceedings of the Third IEEE International Conference on Nano/Micro Engineered and Molecular Systems, Jan. 6-9, 2008, Sanya, China, pp. 921-926, (6 Pages Total).

*Primary Examiner* — Bhisma Mehta
*Assistant Examiner* — John J Crawford
(74) *Attorney, Agent, or Firm* — Dickinson Wright PLLC

(57) ABSTRACT

An attachable needle assembly (2) is disclosed for use on a medication delivery pen (4). The needle assembly (2) includes a housing (8) enclosing a hub (12) that is configured to engage the medication delivery pen (4), a plurality of needles (18) configured to pierce a reservoir septum (6) of the medication delivery pen (4), a selection ring insert (30) that rotates and identifies which needle (24) of the plurality (Continued)

of needles (18) is to be selected, and a selection ring (36) that applies a force to expose the selected needle (24). When the housing (8) is in a first position, the plurality of needles (18) is not exposed, and when the housing (8) is in a second position, one of the plurality of needles (24) is exposed for medicament delivery.

21 Claims, 11 Drawing Sheets

(51) Int. Cl.
  *A61M 5/34* (2006.01)
  *A61M 5/24* (2006.01)
(52) U.S. Cl.
  CPC ........ *A61M 5/3297* (2013.01); *A61M 5/3298* (2013.01); *A61M 5/34* (2013.01); *A61M 5/3293* (2013.01); *A61M 2005/004* (2013.01); *A61M 2205/18* (2013.01)
(58) Field of Classification Search
  CPC .......... A61M 5/3293; A61M 2005/004; A61M 2205/18; A61M 5/002
  See application file for complete search history.

(56) References Cited

U.S. PATENT DOCUMENTS

| | | |
|---|---|---|
| 5,931,817 A | 8/1999 | Nguyen et al. |
| 8,876,780 B2 | 11/2014 | Bruehwiler et al. |
| 9,101,724 B2 | 8/2015 | Chapin et al. |
| 9,107,988 B2 | 8/2015 | Bruehwiler et al. |
| 9,155,838 B2 | 10/2015 | Bilton et al. |
| 9,381,303 B2 | 7/2016 | Abhijitsinh et al. |
| 9,717,860 B2 | 8/2017 | Bruehwiler et al. |
| 10,029,042 B2 | 7/2018 | Searle et al. |
| 2001/0014792 A1 | 8/2001 | West et al. |
| 2002/0020646 A1 | 2/2002 | Groth et al. |
| 2002/0020647 A1 | 2/2002 | Groth |
| 2005/0084631 A1 | 4/2005 | Anderson |
| 2008/0312604 A1 | 12/2008 | Boesen |
| 2010/0217206 A1 | 8/2010 | Lum et al. |
| 2011/0068034 A1 | 3/2011 | Hwang et al. |
| 2012/0004620 A1 | 1/2012 | Spool et al. |
| 2012/0016315 A1 | 1/2012 | Radmer et al. |
| 2012/0041373 A1* | 2/2012 | Bruehwiler ......... A61M 5/3205 604/173 |
| 2012/0041381 A1 | 2/2012 | Raj et al. |
| 2012/0041383 A1* | 2/2012 | Bruehwiler ........... A61M 5/008 604/192 |
| 2012/0041390 A1 | 2/2012 | Spool et al. |
| 2013/0041321 A1 | 2/2013 | Cross et al. |
| 2013/0053751 A1 | 2/2013 | Holtham |
| 2014/0076758 A1 | 3/2014 | Dasbach et al. |
| 2014/0123479 A1 | 5/2014 | Dasbach |
| 2014/0262884 A1 | 9/2014 | Priebe et al. |
| 2014/0299622 A1 | 10/2014 | Hofmann et al. |
| 2014/0332425 A1 | 11/2014 | Hofmann et al. |
| 2014/0339113 A1* | 11/2014 | Hofmann ............. A61M 5/3205 206/366 |
| 2015/0025469 A1 | 1/2015 | Larsen et al. |
| 2015/0163898 A1 | 6/2015 | Mokhtarzad |
| 2015/0283333 A1 | 10/2015 | Butler et al. |
| 2015/0335827 A1* | 11/2015 | Stefansen ............. A61M 5/343 604/173 |
| 2015/0346184 A1 | 12/2015 | Galasso |
| 2016/0000992 A1* | 1/2016 | Steel ..................... A61M 5/002 604/198 |
| 2016/0030683 A1 | 2/2016 | Taylor et al. |
| 2016/0074587 A1 | 3/2016 | Searle et al. |
| 2016/0082195 A1 | 3/2016 | Atterbury et al. |
| 2016/0106925 A1 | 4/2016 | Boesen |

FOREIGN PATENT DOCUMENTS

| | | |
|---|---|---|
| EP | 2428236 A1 | 3/2012 |
| EP | 2586475 A1 | 5/2013 |
| EP | 2604304 A1 | 6/2013 |
| EP | 2696913 B1 | 9/2015 |
| WO | 2008/150715 A1 | 12/2008 |
| WO | WO-2011083055 A1 | 7/2011 |
| WO | 2014/020001 A1 | 2/2014 |
| WO | 2016/050902 A1 | 4/2016 |

* cited by examiner

PEN NEEDLE MAGAZINE

This application claims the benefit under 35 U.S.C. § 119(e) of U.S. Provisional Patent Application Ser. 62/328,655, filed on Apr. 28, 2016, which is hereby incorporated by reference in its entirety.

FIELD

Various exemplary embodiments of the invention relate to medication pens.

BACKGROUND

Medication pens are typically used to inject medication into a patient. A person who must periodically self-inject doses of medication will typically carry a medication pen and several single-use pen needles. A medication pen is designed for safety and sterility. However, inefficiencies and inconveniences arise.

SUMMARY OF THE INVENTION

It is an aspect of the present invention to provide a needle assembly that is attachable to a medication pen to provide a magazine of needles for use. Such a needle assembly provides advantages in separating a patient end and a non-patient end and allows for engagement and disengagement. Moreover, improvements in sterility and simplicity are achieved by the needle assembly such that all the needles in the magazine are always piercing a vial, cartridge or reservoir septum of the medication pen, each needle is used for injection one at a time, and each needle only moves axially.

Having a magazine of needles available for medication delivery reduces needle reuse. Needle reuse is undesired for at least the following reasons. The needle dulls after a single use and so subsequent use may cause pain to the patient. Multiple needle use can also reduce the strength of the needle tip which may cause a potential fracture. Also, needle reuse increases sanitary concerns and health risks to the patient.

The needle assembly of the present invention advantageously reduces reuse for at least the following reason. Although patients may desire to financially benefit from using a needle multiple times, the needle assembly is configured to prevent each of the plurality of needles from being used more than once. Convenience is another reason patients reuse needles. Patients may also be concerned about not having another needle available for use or not having access to supplies. However, the needle assembly conveniently provides multiple needles so that an unused needle is more readily available.

The foregoing and/or other aspects of the present invention can be achieved by providing an attachable needle assembly for use on a medication delivery pen, the needle assembly comprising a housing enclosing a hub that is configured to engage the medication delivery pen, a plurality of needles configured to pierce a vial, cartridge or reservoir septum of the medication delivery pen, a selection ring insert that rotates and identifies which needle of the plurality of needles is to be selected, and a selection ring that applies a force to expose the selected needle, wherein when the housing is in a first position, the plurality of needles is not exposed, and when the housing is in a second position, one of the plurality of needles is exposed for medicament delivery.

The foregoing and/or other aspects of the present invention can also be achieved by a method of operating an attachable needle assembly of a medication delivery pen, the method comprising connecting the medication delivery pen to a housing of the attachable needle assembly, piercing a vial, cartridge or reservoir septum of the medication delivery pen with a plurality of needles of the needle assembly, rotating a selection ring insert to identify which needle of the plurality of needles is to be selected, and applying a force, by a selection ring, to the selected needle to expose the selected needle, wherein when the housing is in a first position, the plurality of needles is not exposed, and when the housing is in a second position, one of the plurality of needles is exposed for medicament delivery.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which.

DETAILED DESCRIPTION OF EXEMPLARY EMBODIMENTS

Figure 1:
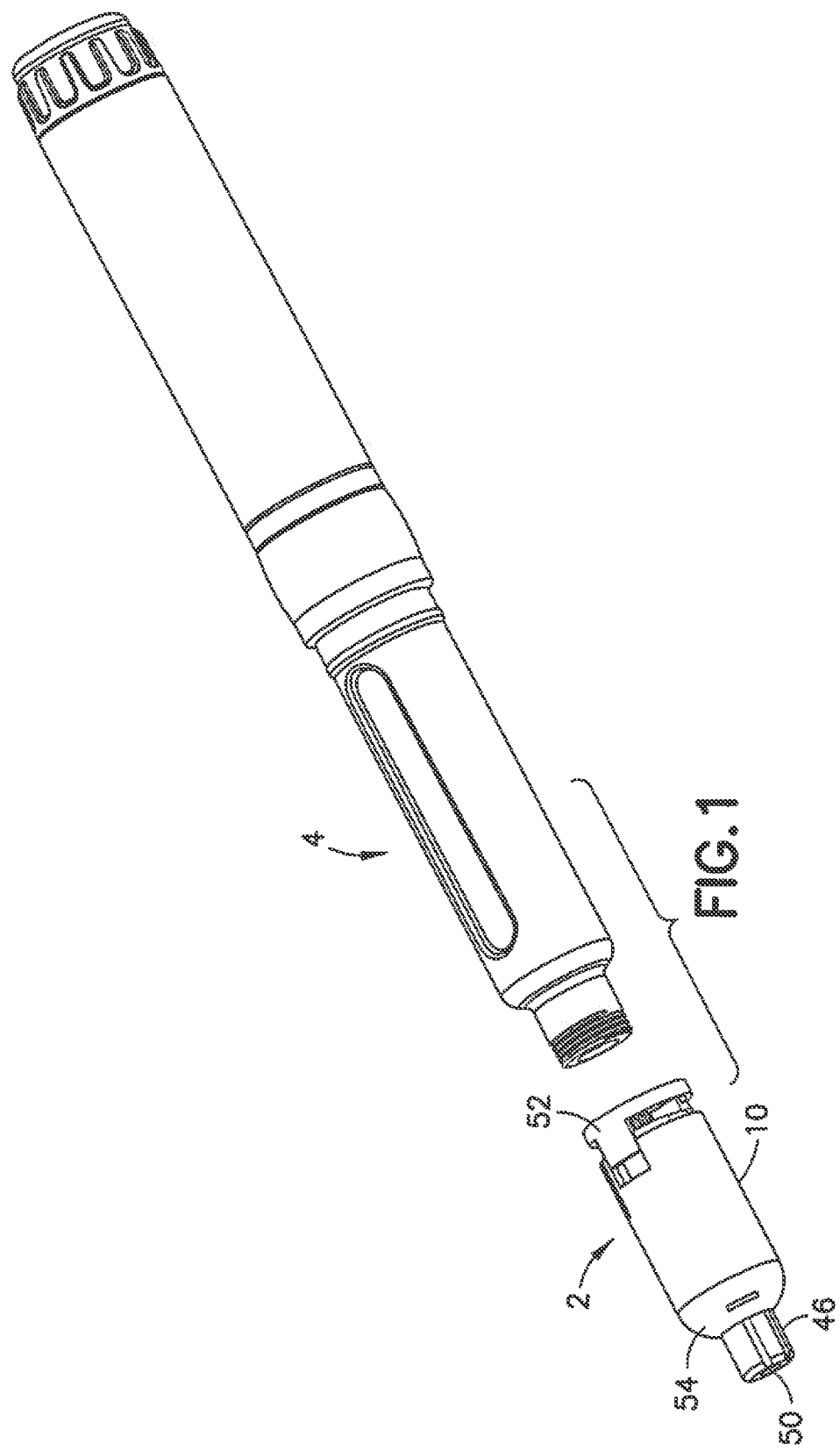
FIG. 1 illustrates a perspective view of an exemplary medication delivery pen and a needle assembly.

FIG. 1 illustrates a typical medication delivery pen 4 used for injecting medicament, such as liquid, drugs, into a living body. A needle assembly 2 is mourned on the medication delivery pen 4 to enhance medication delivery. Benefits and advantages of the needle assembly 2 are described below.

Figure 2:
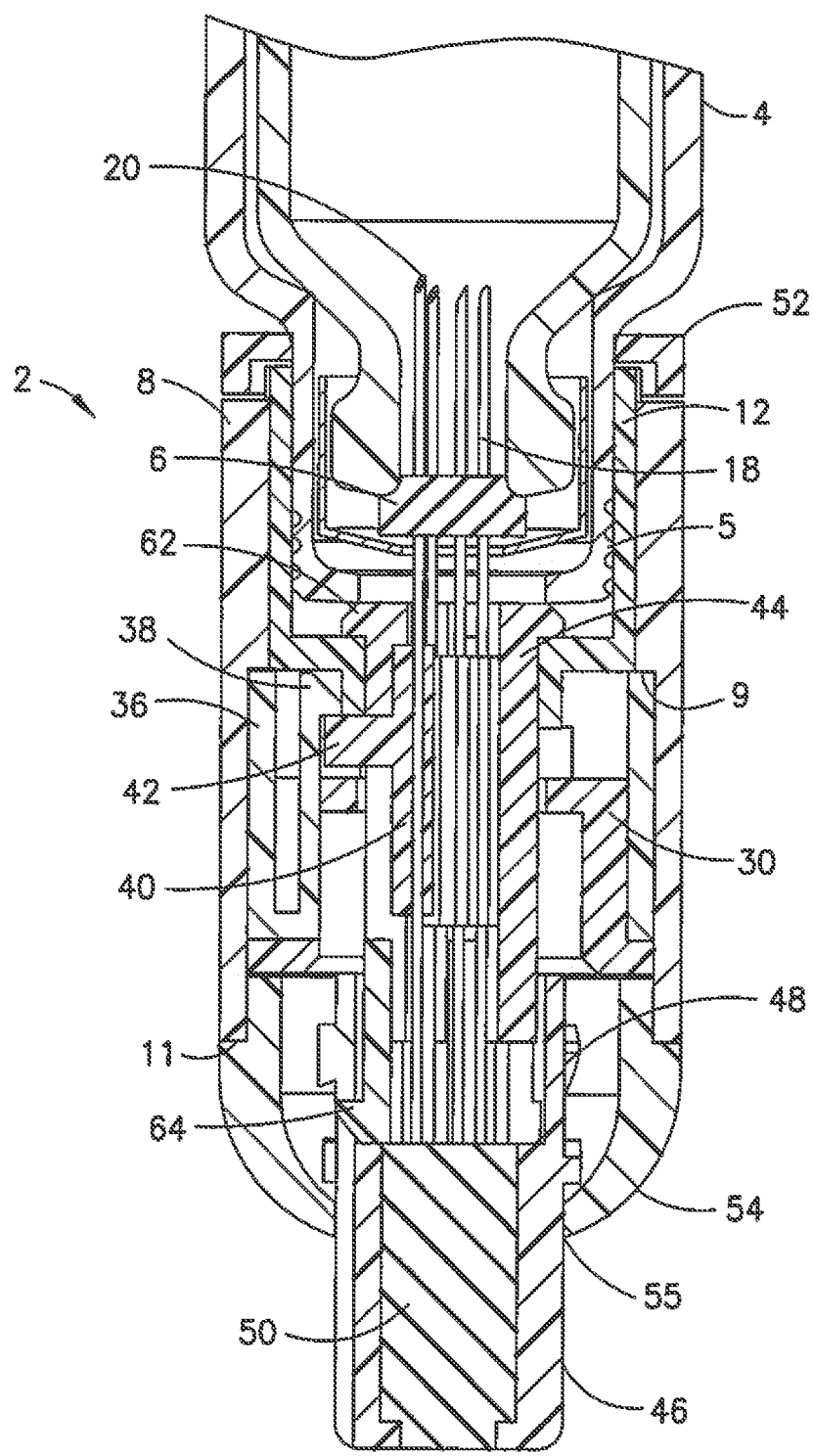
FIG. 2 illustrates a cross sectional view of the needle assembly in a first position.
Figure 3:
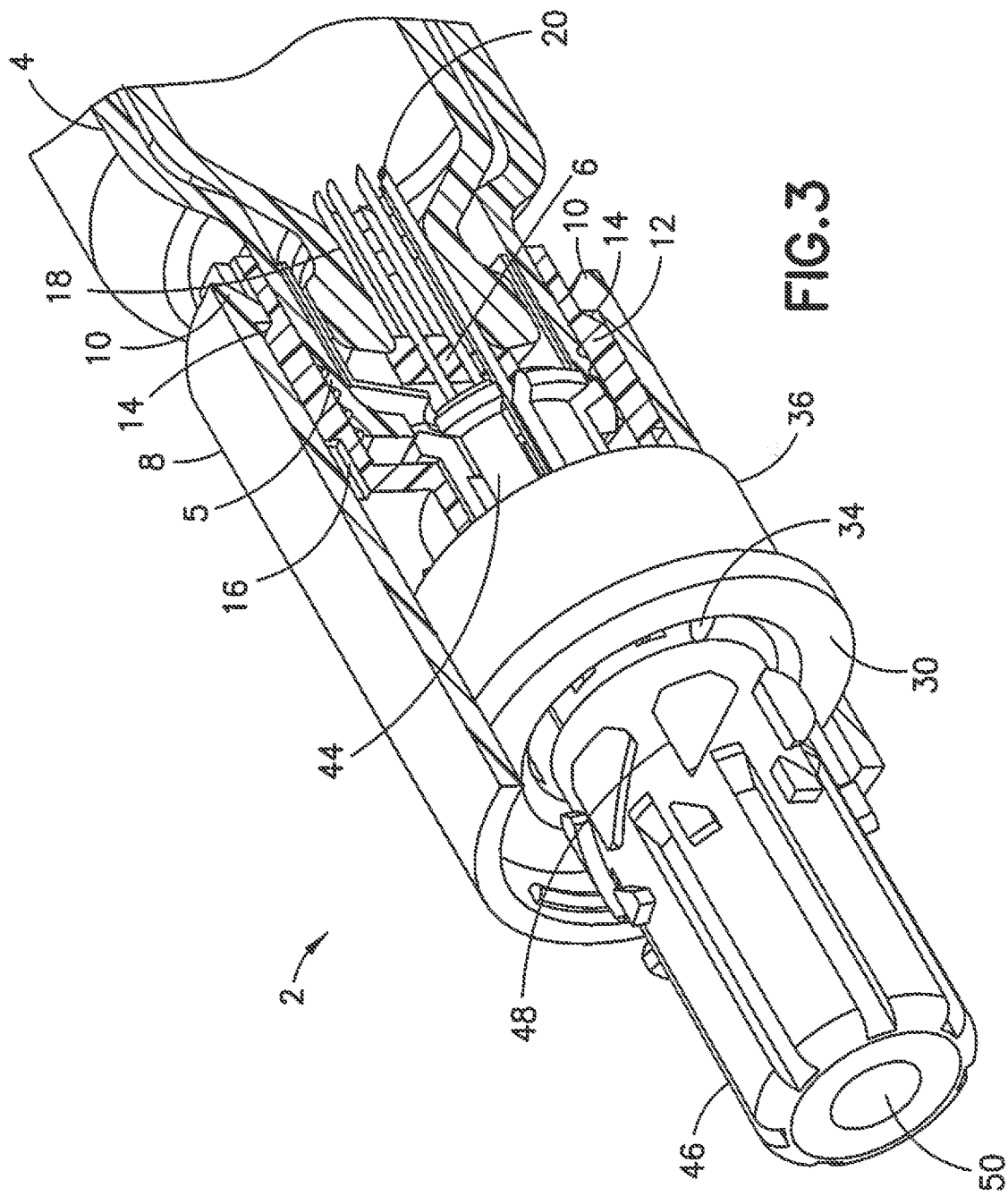
FIG. 3 illustrates a partial cross sectional view of the needle assembly in the first position.
Figure 6:
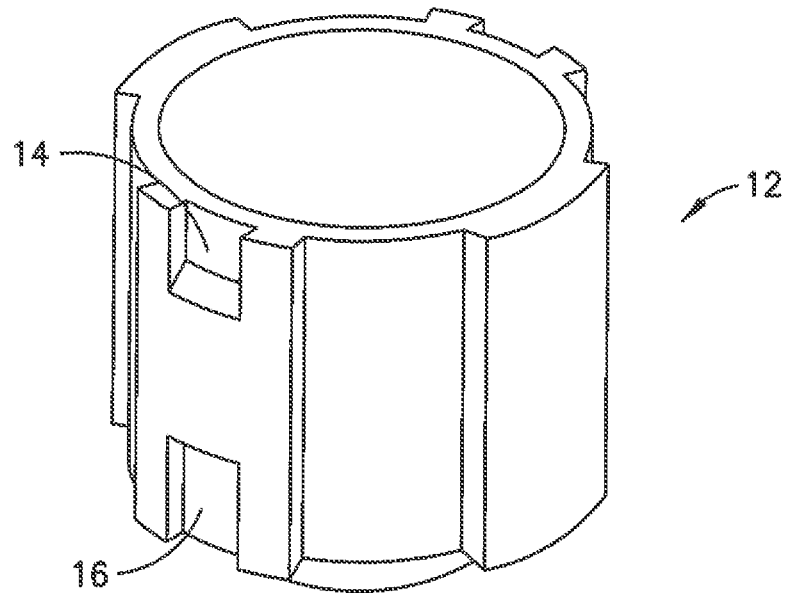
FIG. 6 illustrates a perspective view of a hub.

According to one embodiment, FIGS. 2 and 3 illustrate the needle assembly 2 mounted on the medication delivery pen 4 prior to operation in a first position. The needle assembly 2 includes a hub 12 having internal threads (not illustrated) that engage external threads 5 on the medication delivery pen 4. The threaded assembly allows a user to attach and detach the needle assembly 2 from the medication delivery pen 4. Although threads are disclosed, a variety of engagement mechanisms are contemplated, such as a press-fit, laser welding or the use of adhesives. According to one embodiment, the hub 12, as further illustrated in FIG. 6, also includes first and second interlocks 14, 16.

An installation guide 52, according to one embodiment, is provided to align the needle assembly 2 to a distal end of the medication delivery pen 4. Specifically, an inner diameter of the installation guide 52 engages an outer diameter of a distal end of the medication delivery pen 4 before a plurality of needles 18 of the needle assembly 2 pierce a vial, cartridge or reservoir septum 6 of the medication delivery pen 4. This configuration advantageously reduces the risk of the plurality of needles 18 being damaged during installation. Also, the installation guide 52 protects the plurality of needles 18 from being damaged accidentally before assembly and protects a user from undesired needle contact.

It is important that the plurality of needles 18 do not rotate as the needle assembly 2 is being attached to the medication delivery pen 4. To avoid rotation of the plurality of needles 18, the needle assembly 2 is configured so that the installation guide 52 rotates with respect to the plurality of needles 18 to attach to the medication delivery pen 4.

Figure 4:
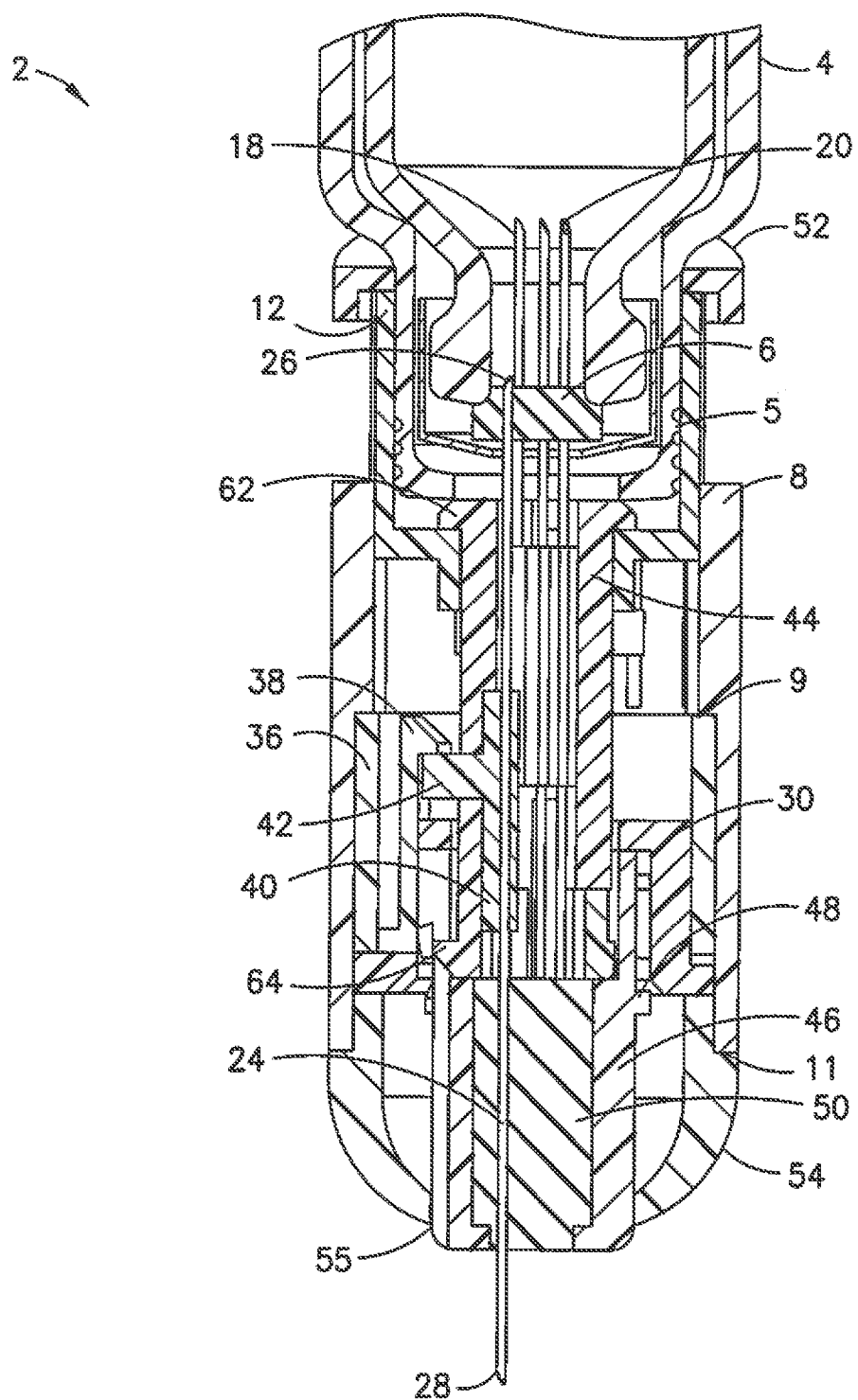
FIG. 4 illustrates a cross sectional view of the needle assembly in a second position.
Figure 5:
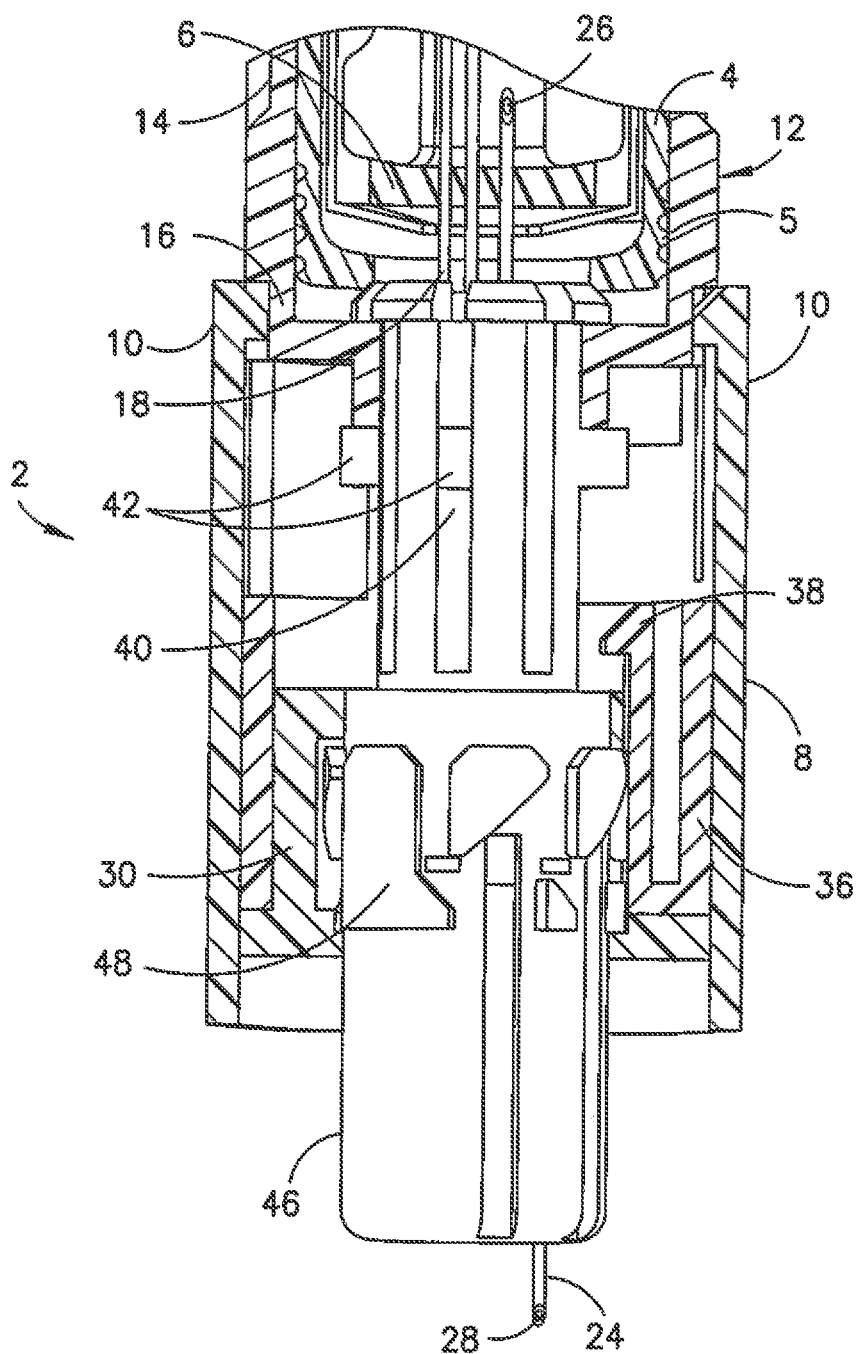
FIG. 5 illustrates a partial cross sectional view of the needle assembly in the second position.

FIGS. 2 and 3 illustrate a housing 8 having a housing flange 10 that encloses the needle assembly 2. The housing flange 10 engages the first interlock 14 in the first position where the needle assembly 2 is not in operation. According to one embodiment, as illustrated in FIGS. 4 and 5, the housing 8 moves to a second position by a user where the housing flange 10 engages the second interlock 16 to withdraw a needle 24 and operate the needle assembly 2 in communication with the medication delivery pen 4. Thus, the housing 8 is rotationally coupled to the hub 12.

The needle assembly 2 acts as a magazine for holding the plurality of needles 18. Preferably, seven hollow needles are disposed in the needle assembly 2, although more or less is contemplated. When the needle assembly 2 is mounted to the medication delivery pen 4, each of the plurality of needles 18 pierces the reservoir septum 6 of the medication delivery pen 4. The needle piercing provides fluid communication between the needle assembly 2 and an insulin cartridge, for example, of the medication delivery pen 4. As illustrated, a proximal end 20 of the plurality of needles 18 is disposed in the insulin cartridge of the medication delivery pen 4 and a sharpened distal end (not shown) of the plurality of needles 18 is disposed inside a septum 50 of the needle assembly 2.

The septum 50 of the needle assembly 2 aids to regulate the dispensing of medicament by sealing the plurality of needles 18 at various times during operation. The septum 50 maintains a sterile environment for the plurality of needles 18 before, during and after use. After a needle is used, the septum 50 encloses the distal tip and protects the distal tip from reuse and injury to a user.

Figure 7:
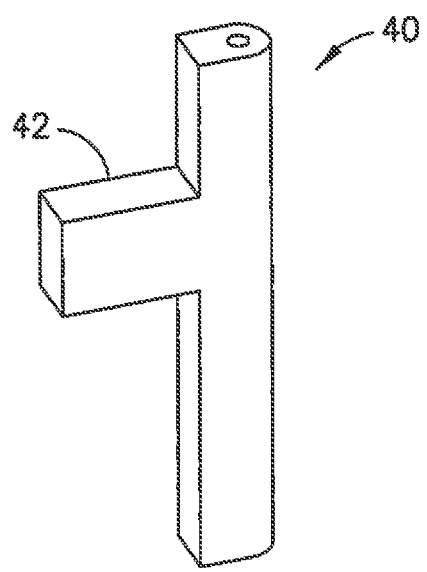
FIG. 7 illustrates a perspective view of a needle post.

According to one embodiment, each of the plurality of needles 18 is secured to a respective needle post 40, as further illustrated in FIG. 7. Each of the plurality of needles 18 is preferably secured to a needle post 40 by an adhesive, such as a medical grade adhesive, but other adhesives and fastening means such as a press fit are contemplated. The adhesive is compatible with the material of the plurality of needles 18 and the material of the plurality of needle posts 40. The plurality of needle posts 40 each include an extending portion 42 that aids in operation of the needle assembly 2 as described below.

Figure 10:
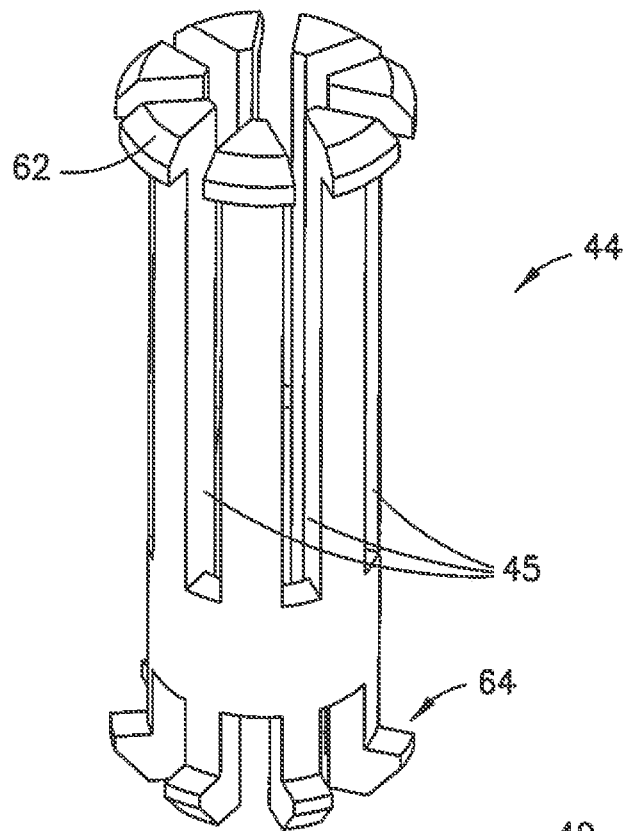
FIG. 10 illustrates a perspective view of a needle guide top.

According to one embodiment, the plurality of needle posts 40 is disposed in a needle guide top 44 as illustrated in FIG. 10. The needle guide top 44 includes a plurality of needle guide slots 45. When each of the plurality of needle posts 40 is assembled into the needle guide top 44, each of the extending portions 42 is disposed and extends through a respective needle guide slot 45. In other words, the needle guide top 44 arranges the plurality of needle posts 40 such that the extending portions 42 extend outward from a centerline of the needle guide top 44. Accordingly, the needle posts 40 are able to slide axially through the needle guide slots 45 and within the needle guide top 44 without obstruction. Moreover, the needle guide slots 45 engage the extending portions 42 of the needle posts 40 and prevent the needle posts 40 from rotating. During assembly prior to operation, an upper portion 62 of the needle guide top 44 snaps into engagement with the hub 12.

The hub 12 engages the needle guide top 44 such that the hub 12 rotates freely with respect to the upper portion of the needle guide top 62. Thus, the hub 12 advantageously rotates independently from the plurality of needle posts 40. Accordingly, when the user connects the needle assembly 2 to the medication delivery pen 4 via threads as described above, the plurality of needles 18 does not rotate with respect to the reservoir septum 6. Instead, the plurality of needles 18 simply translates axially through the reservoir septum 6. Rotation of the plurality of needles 18 when the needle assembly 2 is mounted on the medication delivery pen 4 is advantageously avoided. Otherwise, damage to the reservoir septum 6 and the plurality of needles 18 may arise.

Figure 9:
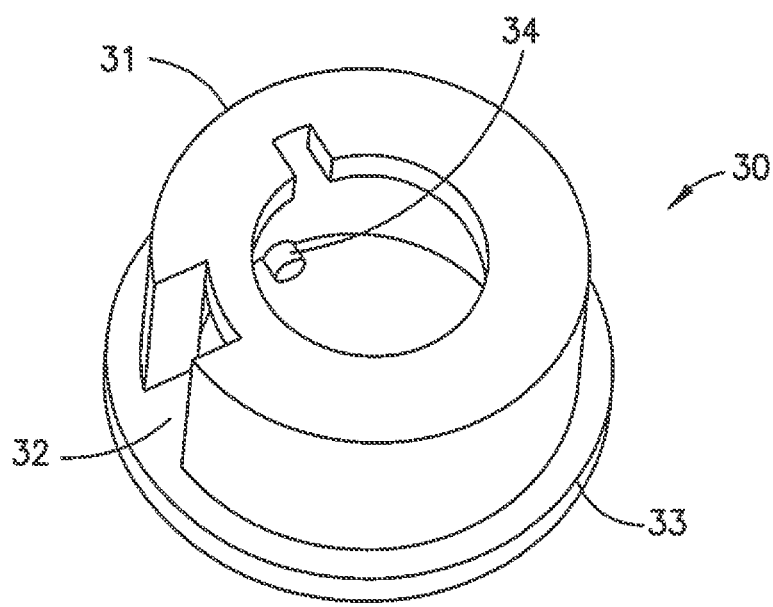
FIG. 9 illustrates a perspective view of a selection ring insert.

The needle assembly 2 further includes a selection ring insert 30 that rotates during operation to identify which needle of the plurality of needles 18 is to be selected. According to one embodiment, the selection ring insert 30 includes an outer cylindrical surface 31 at a first diameter, a bottom surface 33 at a second diameter and a generally hollow interior. The first diameter is smaller than the second diameter. According to one embodiment, as illustrated in FIG. 9, the selection ring insert 30 includes a notch 32 and a follower 34. The notch 32 is provided on the outer cylindrical surface 31 of the selection ring insert 30 to engage a selection ring 36. The follower 34 is a protrusion at the interior of the selection ring insert 30 that guides the rotation of the selection ring insert 30. Operation of the notch 32 and the follower 34 are described below.

Figure 8:
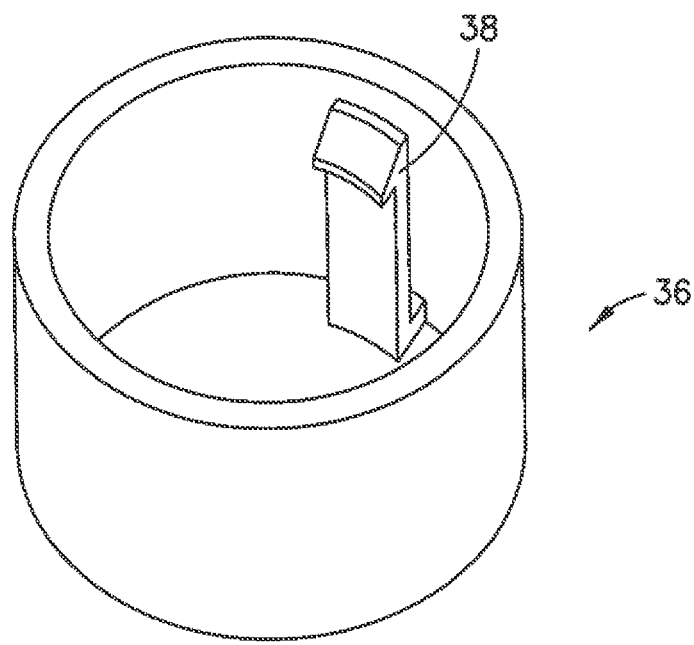
FIG. 8 illustrates a perspective view of a selection ring.

The selection ring 36, according to one embodiment illustrated in FIGS. 2, 3 and 8, is disposed over the outer cylindrical surface 31 of the selection ring insert 30. The selection ring 36 includes a selection ring flange 38 and a chamfer. The selection ring flange 38 is disposed in the notch 32 of the selection ring insert 30 for engagement and to cause the selection ring insert 30 and the selection ring 36 to rotate together. The chamfer allows the selection ring flange 38 of the selection ring 36 to radially deflect and snap over the needle post 40 of the selected needle 24 when the needle assembly 2 travels from the second position to the first position. During assembly, the selection ring 36 contacts an inner wall 9 of the housing 8. In operation, the selection ring flange 38 contacts the extending portion 42 of the needle post 40 and applies a force to expose a selected needle. The selection ring 36 rotates with respect to the housing 8 but moves axially with the housing 8.

Figure 11:
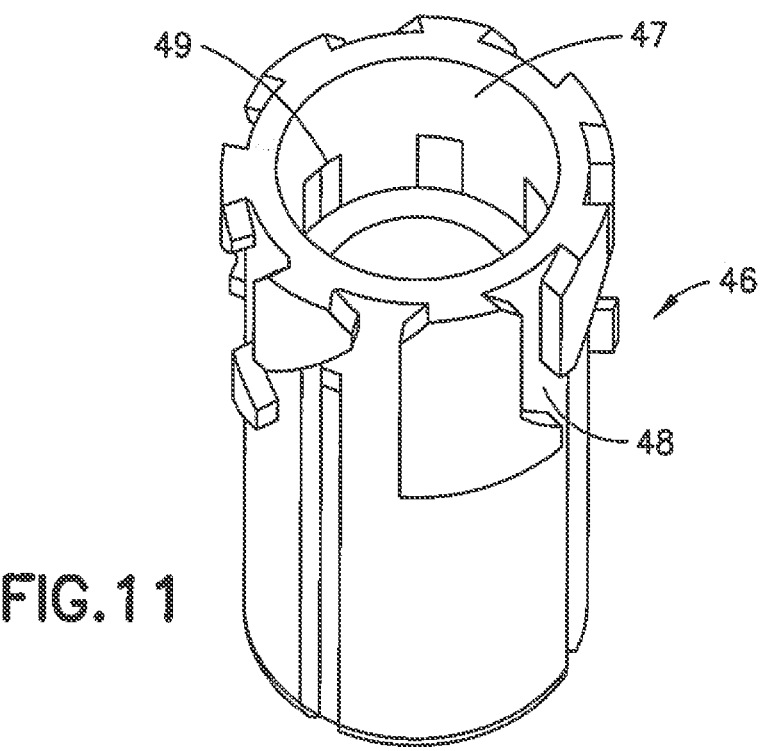
FIG. 11 illustrates a perspective view of a needle guide.

According to one embodiment as illustrated in FIG. 11, the needle assembly 2 also includes a needle guide 46. The needle guide 46 includes an inner cavity 47 that supports a portion of the needle guide top 44 and the septum 50 of the needle assembly 2. During assembly, the needle guide 46 includes recesses 49 along an inner surface of the inner cavity 47 to engage a lower portion 64 of the needle guide top 44.

The needle guide 46 also includes a plurality of curvilinear paths 48 disposed along an outer surface of the needle guide 46. The curvilinear paths 48 comprise a variety of protruded surfaces along the outer surface of the needle guide 46 that create an inscribed passageway to engage the follower 34 of the selection ring insert 30.

According to an alternate embodiment, the follower 34 is disposed on the outer surface of the needle guide 46 and the curvilinear paths 48 are disposed on the interior of the selection ring insert 30. Moreover, a variety of configurations such as tracks and slides are contemplated.

The needle assembly 2, according to one embodiment, further includes a cap 54 secured to the housing 8. The cap 54 and the housing 8 support all the components of the needle assembly 2. In assembly, the cap 54 engages the housing 8 via a snap-fit joint, for example, and contacts a bottom wall 11 of the housing 8. Also, the cap 54 includes a hole 55 at its distal end allowing the needle guide 46 to enter into. The hole 55 is sized to prevent the needle guide 46 from exiting the cap 54 and to reduce tampering.

According to one embodiment, FIGS. 4 and 5 illustrate the housing 8 in the second position where a selected needle 24 amongst the plurality of needles 18 is exposed for medicament delivery. FIGS. 12-16 illustrate a subassembly of the needle guide 46 and the selection ring insert 30 that show the various steps of moving between the first and second positions.

Figure 12:
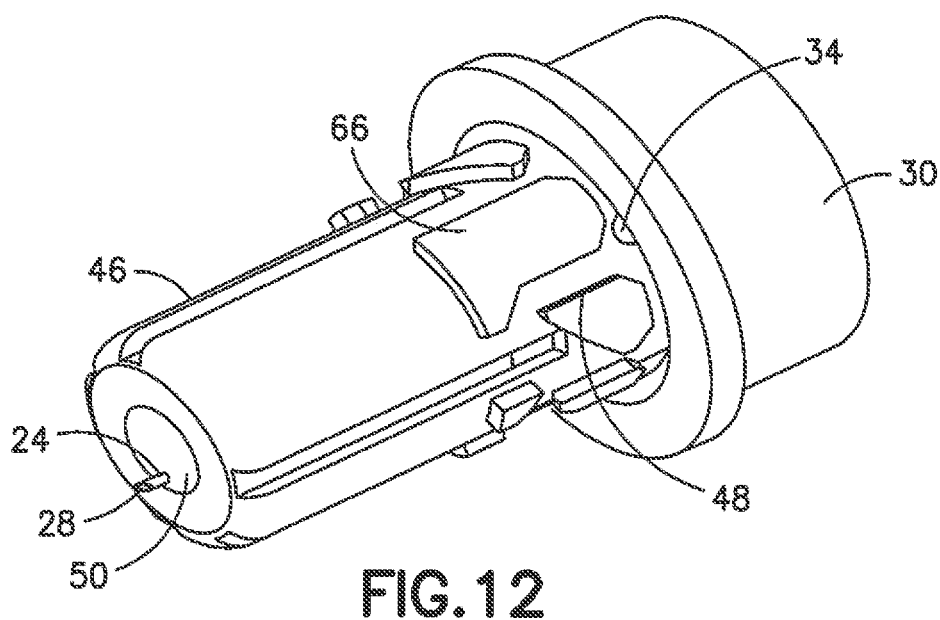
FIG. 12 illustrates a perspective view of the selection ring insert and the needle guide beginning to leave the first position.

Specifically, FIG. 12 illustrates the selection ring insert 30 and the needle guide 46 beginning to move from the first position. The follower 34 of the selection ring insert 30 is not engaged to the curvilinear path 48 of the needle guide 46. As the needle assembly 2 leaves the first position, the selected needle 24 begins to pierce the sealing septum 50 and the remaining plurality of needles 18 are all sealed and sterilized in the septum 50 of the needle assembly 2.

Figure 13:
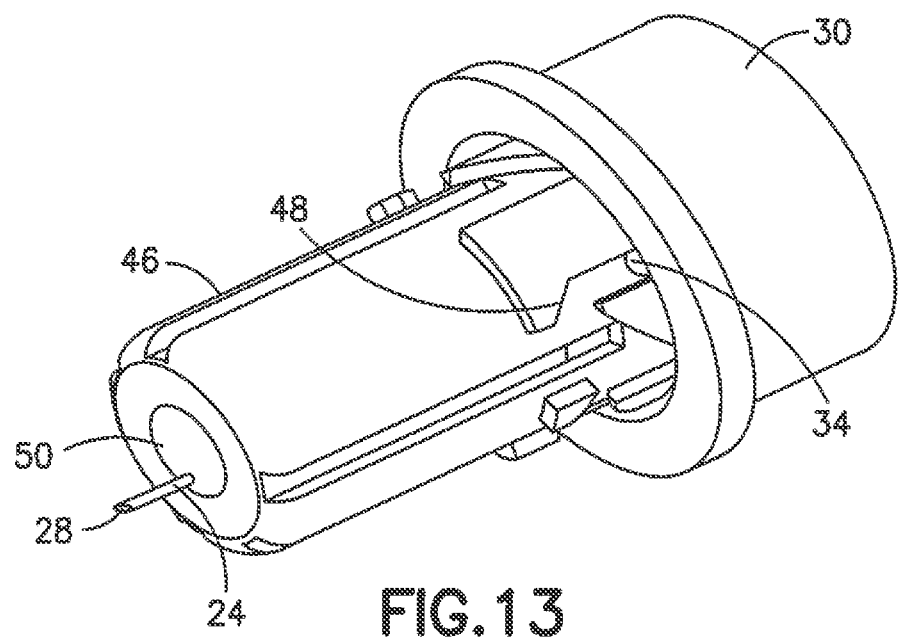
FIG. 13 illustrates a perspective view of the selection ring insert and the needle guide where the selection ring insert is traveling toward the second position from the first position.

As the user pulls the housing 8 from the first position, FIG. 13 illustrates the follower 34 of the selection ring insert 30 entering into the curvilinear path 48 of the needle guide 46. The curvilinear path 48 gradually causes the selection ring insert 30 to rotate with respect to the needle guide 46 and the housing 8. The inner housing wall 9 of the housing 8 contacts the selection ring 36 and causes the selection ring insert 30 to axially move with the housing 8. When the selection ring insert 30 axially moves toward the second position, the selection ring insert 30 also rotates as the follower 34 travels along the curvilinear path 48 of the needle guide. Since the selection ring 36 is rotationally coupled to the selection ring insert 30, the flange 38 of the selection ring 36 pulls the extending portion 42 of the needle post 40 of the selected needle 24 causing the distal end 28 of the selected needle 24 to pierce the septum 50 of the needle assembly 2 and expose the selected needle 24 for medication delivery.

Figure 14:
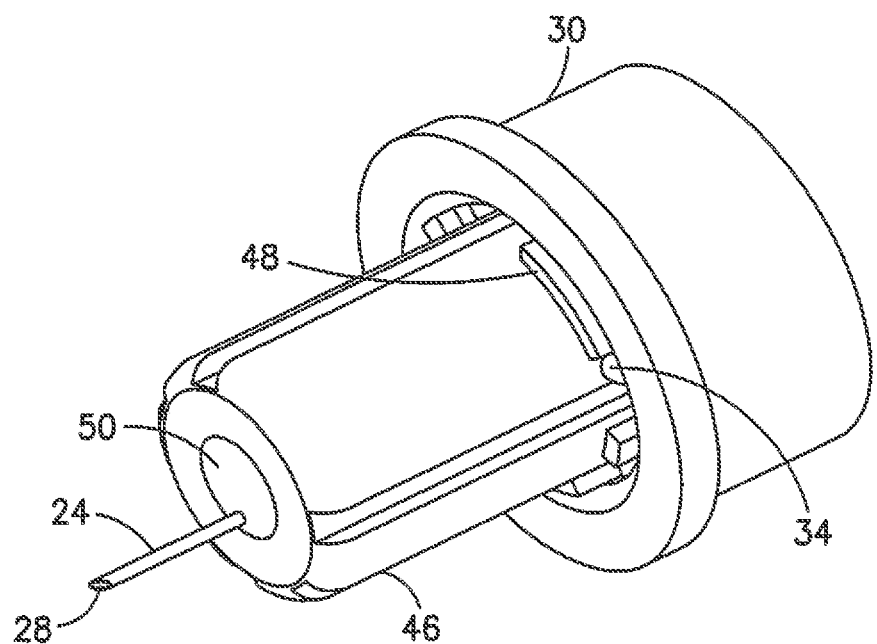
FIG. 14 illustrates a perspective view of the selection ring insert and the needle guide in the second position.

FIG. 14 illustrates the subassembly in the second position when the user pulls the housing 8 away from the medication delivery pen 4. Specifically, the follower 34 is at the end of the curvilinear path 48. In this position, as illustrated in FIGS. 4 and 5, the distal end 28 of the selected needle 24 extends beyond the septum 50 of the needle assembly 2 in a fully extended state and the needle assembly 2 is ready for medication delivery. The proximal end 26 of the selected needle 24 continues to pierce the reservoir septum 6 and maintains fluid communication with medication delivery pen 4 to administer the medication.

The proximal end 20 of the remaining needles 18 continues to pierce the reservoir septum 6 and remain in fluid communication with the medication delivery pen 4. The distal end of the remaining needles 18 also continues to stay sealed and sterilized in the septum 50 of the needle assembly 2.

During operation, although the selected needle 24 moves axially, the selected needle 24 does not move radially. In fact, none of the plurality of needles 18 substantially moves radially or rotates at any point during operation. No substantial radial or rotational movement in this regard is understood as 0±5% with respect to a centerline of the needle assembly 2. Preferably, one skilled in the art understands that substantial in this context means that no radial or rotational movement is required to perform the intended function. However, slight radial or rotational movement may be desired to ensure the proper spacing of parts for smooth operation and proper movement of the needles axially without jamming. This configuration improves simplicity of the design and reduces movement of parts in the needle assembly 2.

The user cannot draw the housing 8 out from the needle assembly 2 any further than the second position of the needle assembly 2 because of the configuration illustrated in FIGS. 3 and 4. Specifically, the housing flanges 10 engage with the second hub interlock 16 to prevent further axial movement of the needle assembly 2. More specifically, the cap 54 and the needle guide 46 contact a patient delivery site during needle insertion and injection.

Figure 15:
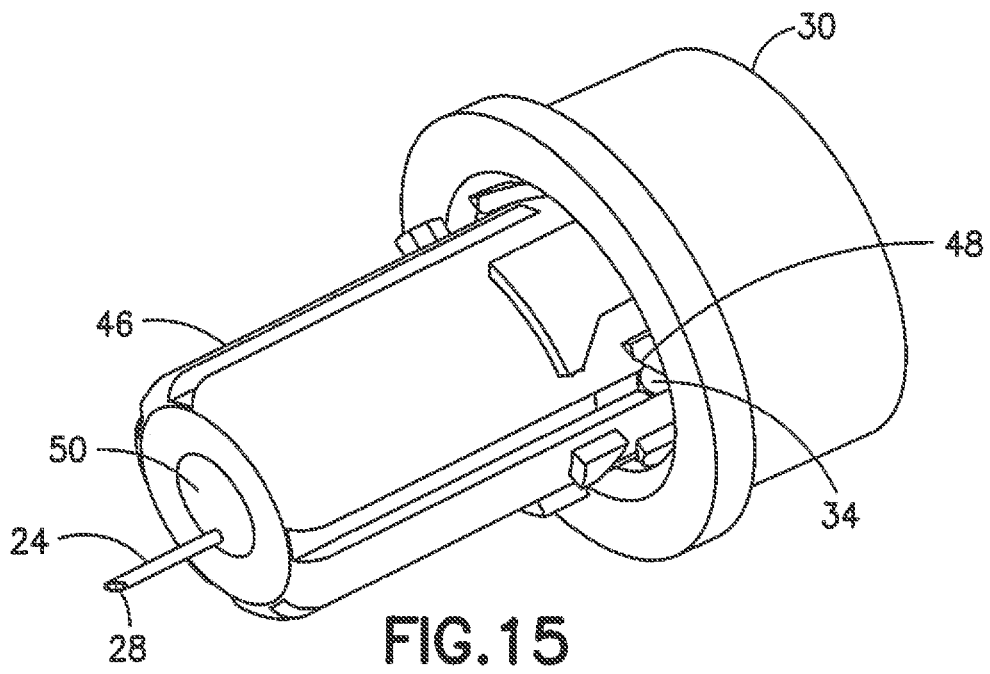
FIG. 15 illustrates a perspective view of the selection ring insert and the needle guide where the selection ring insert is traveling toward the first position from the second position.

FIG. 15 illustrates the subassembly returning from the second position back to the first position when the user pushes the housing 8 back toward the medication delivery pen 4. The cap 54 pushes the selection ring insert 30 upwards which moves the extending portion 42 of the selected needle 24 upward. The distal end 28 of the selected needle 24 returns into the septum 50 of the needle assembly 2. The septum 50 sterilizes the selected needle 24 and protects the user. Meanwhile, the follower 34 enters into a different curvilinear path 48 so that the selection ring insert 30 continues to rotate and prepare the flange 38 of the selection ring 36 to align with an adjacent needle of the plurality of needles 18 for a subsequent injection. Specifically, the chamfer of the selection ring 36 allows the flange 38 to radially deflect and snap over the needle post 40 of the adjacent needle of the plurality of needles 18 when the needle assembly 2 travels from the second position to the first position.

Figure 16:
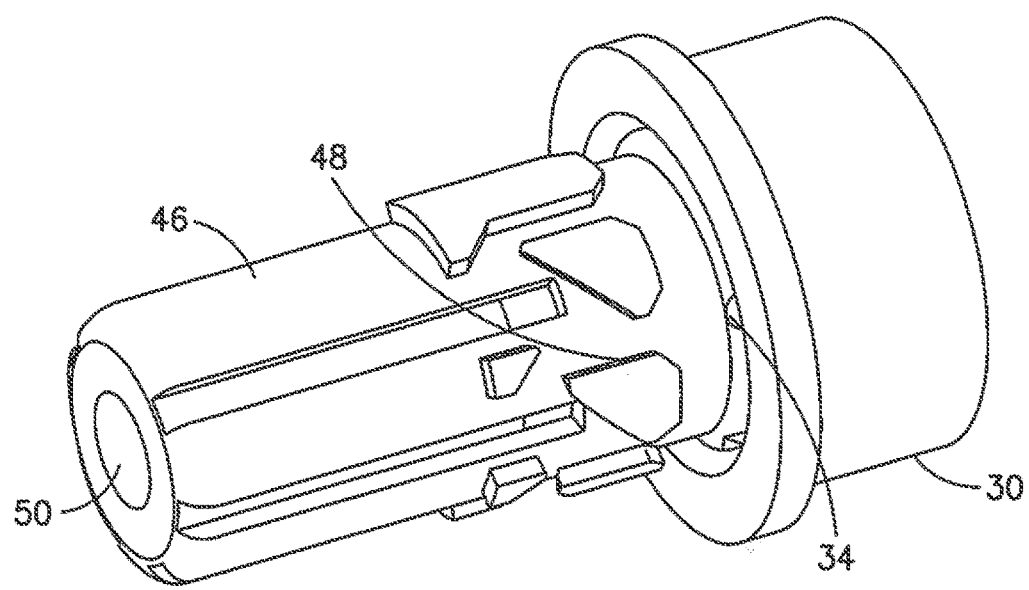
FIG. 16 illustrates a perspective view of the selection ring insert and the needle guide where the selection ring insert returns to the first position.

FIG. 16 illustrates the subassembly back to the first position where the distal ends of all the needles 18 are retracted and disposed in the septum 50 of the needle assembly 2. The flange 38 of the selection ring 36 is now rotated and aligned to push the extending portion 42 of the needle post 40 of the subsequent needle amongst the plurality of needles 18 when the housing 8 moves from the first position to the second position.

The process of moving from the first position to the second position and back to the first position while rotating the selection ring 36 repeats so that each needle amongst the plurality of needles 18 is individually exposed in a consecutive manner from a first needle, to each adjacent needle and to a last needle. Additionally, as illustrated in FIG. 12, the curvilinear path 48 includes a large protruded surface 66 that causes the last needle of the plurality of needles 18 to be continuously selected and reused. In other words, when the selection ring 36 engages the last needle of the plurality of needles 18, the curvilinear path 48 is configured not to rotate the selection ring insert 30 any further. This configuration advantageously provides a means for repeated use of the last needle in the needle assembly 2 after each of the other needles 18 is used only once.

Figure 17:
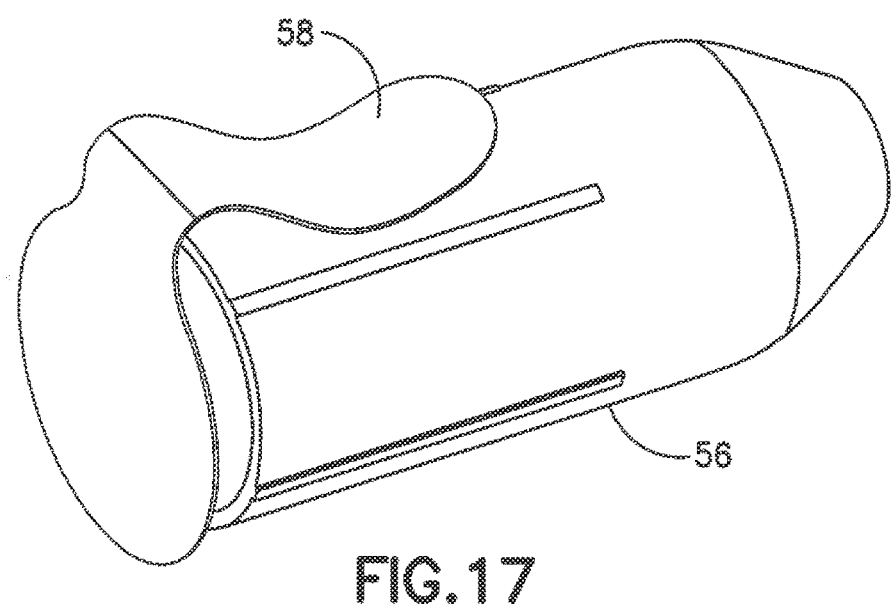
FIG. 17 illustrates a perspective view of the needle assembly in a cover and sealed by a teardrop label.

FIG. 17, according to one embodiment, illustrates a cover 56 that encloses the needle assembly 2. The cover 56 is sealed with a teardrop label 58 to seal the needle assembly 2 and maintain its sterility for transportation and security purposes prior to operating with the medication delivery pen 4. When the needle assembly 2 is ready for use, the user peels off the teardrop label 58 and removes the needle assembly 2 from the cover 56.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. An attachable needle assembly for use on a medication delivery pen, the needle assembly comprising:
a housing enclosing:
a hub that is configured to engage the medication delivery pen;
a plurality of needles configured to pierce a reservoir septum of the medication delivery pen;
a selection ring insert that rotates and identifies which needle of the plurality of needles is to be selected; and
a selection ring that applies a force to expose the selected needle, wherein
when the housing is in a first position, the plurality of needles is not exposed;
when the housing is in a second position, the selected needle is exposed for medicament delivery; and
when the housing is in the first position, each of the plurality of needles are configured to simultaneously pierce the reservoir septum of the medication delivery pen.

2. The attachable needle assembly of claim 1, wherein the selection ring insert rotates with respect to the housing and moves axially with the housing when the housing travels from the first position to the second position and returns to the first position.

3. The attachable needle assembly of claim 1, wherein the hub engages and secures the housing at each of the first and second positions.

4. The attachable needle assembly of claim 1, wherein the plurality of needles includes seven needles.

5. The attachable needle assembly of claim 1, further including
a cover enclosing the needle assembly; and
a label sealing and maintaining sterility of the needle assembly prior to operation.

6. The attachable needle assembly of claim 1, wherein the selection ring is in contact with the selection ring insert.

7. The attachable needle assembly of claim 1, wherein the selection ring moves with the selection ring insert when the housing moves from the first position to the second position.

8. An attachable needle assembly for use on a medication delivery pen, the needle assembly comprising:
a housing enclosing:
a hub that is configured to engage the medication delivery pen;
a plurality of needles configured to pierce a reservoir septum of the medication delivery pen;
a selection ring insert that rotates and identifies which needle of the plurality of needles is to be selected; and
a selection ring that applies a force to expose the selected needle, wherein
when the housing is in a first position, the plurality of needles is not exposed;
when the housing is in a second position, the selected needle is exposed for medicament delivery;
each of the plurality of needles is secured to a respective needle post of a plurality of needle posts; and
the selection ring includes a flange that contacts one of the plurality of needle posts to expose a distal end of the selected needle when the housing is in the second position.

9. The attachable needle assembly of claim 8, wherein the selection ring insert includes a notch that mates with the flange of the selection ring.

10. The attachable needle assembly of claim 8, further comprising
a needle guide top that houses the plurality of needle posts; and
the plurality of needle posts each include an extending portion, wherein
the needle guide top arranges the plurality of needle posts such that the extending portions extend outward from a centerline of the needle guide top.

11. An attachable needle assembly for use on a medication delivery pen, the needle assembly comprising:
a housing enclosing:
a hub that is configured to engage the medication delivery pen;
a plurality of needles configured to pierce a reservoir septum of the medication delivery pen;

a selection ring insert that rotates and identifies which needle of the plurality of needles is to be selected; and a selection ring that applies a force to expose the selected needle, wherein when the housing is in a first position, the plurality of needles is not exposed;

when the housing is in a second position, the selected needle is exposed for medicament delivery;

the selection ring insert includes a follower comprising a protrusion;

the plurality of needles are disposed in a needle guide, the needle guide having a curvilinear path, and the follower travels along the curvilinear path to rotate the selection ring insert.

12. The attachable needle assembly of claim 11, wherein the curvilinear path rotates the selection ring insert to select each needle consecutively from a first needle to a last needle of the plurality of needles.

13. The attachable needle assembly of claim 11, wherein the curvilinear path is configured to cause the selection ring insert to select and continuously reuse a last needle of the plurality of needles.

14. An attachable needle assembly for use on a medication delivery pen, the needle assembly comprising:

a housing enclosing:
  a hub that is configured to engage the medication delivery pen;
  a plurality of needles configured to pierce a reservoir septum of the medication delivery pen;
  a selection ring insert that rotates and identifies which needle of the plurality of needles is to be selected;
  a septum of the needle assembly that maintains a sterile environment and seals the plurality of needles; and
  a selection ring that applies a force to expose the selected needle, wherein when the housing is in a first position, the plurality of needles is not exposed;

when the housing is in a second position, the selected needle is exposed for medicament delivery; and when the housing is in the first position, a proximal end of each of the plurality of needles penetrates the reservoir septum of the medication delivery pen, and a distal end of each of the plurality of needles is disposed in the septum of the needle assembly.

15. The attachable needle assembly of claim 14, wherein when the housing is in the second position, the distal end of each of a remaining plurality of needles is disposed in the septum of the needle assembly.

16. The attachable needle assembly of claim 14, wherein when the housing is in the second position, the proximal end of the selected needle continues to penetrate the reservoir septum of the medication delivery pen and the distal end of the selected needle extends beyond the septum of the needle assembly.

17. An attachable needle assembly for use on a medication delivery pen, the needle assembly comprising:

a housing enclosing:
  a hub that is configured to engage the medication delivery pen;
  a plurality of needles configured to pierce a reservoir septum of the medication delivery pen;
  a selection ring insert that rotates and identifies which needle of the plurality of needles is to be selected; and
  a selection ring that applies a force to expose the selected needle, wherein when the housing is in a first position, the plurality of needles is not exposed;

when the housing is in a second position, the selected needle is exposed for medicament delivery; and the housing moves from the first position to the second position by traveling away from the medication delivery pen.

18. An attachable needle assembly for use on a medication delivery pen, the needle assembly comprising:

a housing enclosing:
  a hub that is configured to engage the medication delivery pen;
  a plurality of needles configured to pierce a reservoir septum of the medication delivery pen;
  a selection ring insert that rotates and identifies which needle of the plurality of needles is to be selected; and
  a selection ring that applies a force to expose the selected needle; wherein when the housing is in a first position, the plurality of needles is not exposed;

when the housing is in a second position, the selected needle is exposed for medicament delivery; and the plurality of needles only moves axially and does not substantially move radially and does not substantially rotate.

19. An attachable needle assembly for use on a medication delivery pen, the needle assembly comprising:

a housing enclosing:
  a hub that is configured to engage the medication delivery pen;
  a plurality of needles configured to pierce a reservoir septum of the medication delivery pen;
  a selection ring insert that rotates and identifies which needle of the plurality of needles is to be selected; and
  a selection ring that applies a force to expose the selected needle; and
  a cap connected to the housing that applies a force to the selection ring insert when the housing is moving from the second position to the first position; wherein when the housing is in a first position, the plurality of needles is not exposed; and when the housing is in a second position, the selected needle is exposed for medicament delivery.

20. A method of operating an attachable needle assembly on a medication delivery pen, the method comprising:

connecting the medication delivery pen to a housing of the attachable needle assembly;

piercing a reservoir septum of the medication delivery pen with a plurality of needles of the needle assembly;

rotating a selection ring insert to identify which needle of the plurality of needles is to be selected; and applying a force, by a selection ring, to the selected needle to expose the selected needle, wherein when the housing is in a first position, the plurality of needles is not exposed;

when the housing is in a second position, the selected needle is exposed for medicament delivery; and wherein the housing moves from the first position to the second position by traveling away from the medication delivery pen.

21. An attachable needle assembly for use on a medication delivery pen, the needle assembly comprising:

a housing enclosing:
  a hub that is configured to engage the medication delivery pen;

a plurality of needles configured to pierce a reservoir septum of the medication delivery pen;

a selection ring insert that rotates and identifies which needle of the plurality of needles is to be selected; and a selection ring that applies a force to expose the selected needle, wherein when the housing is in a first position, the plurality of needles is not exposed;

when the housing is in a second position, the selected needle is exposed for medicament delivery; and when the housing is in the second position, each of the plurality of needles are configured to simultaneously pierce the reservoir septum of the medication delivery pen.

* * * * *